(12) United States Patent
Kumar T. K. et al.

(10) Patent No.: US 10,485,833 B2
(45) Date of Patent: Nov. 26, 2019

(54) XANTHOPHYLL COMPOSITION CONTAINING MACULAR PIGMENTS AND A PROCESS FOR ITS PREPARATION

(75) Inventors: Sunil Kumar T. K., Angamally South (IN); Sherena P. Abdulkadir, Angamally South (IN)

(73) Assignee: OmniActive Health Technologies Limited, Mumbai (IN)

( * ) Notice: Subject to any disclaimer, the term of this patent is extended or adjusted under 35 U.S.C. 154(b) by 105 days.

(21) Appl. No.: 12/874,636

(22) Filed: Sep. 2, 2010

(65) Prior Publication Data
US 2011/0065805 A1    Mar. 17, 2011

Related U.S. Application Data

(60) Provisional application No. 61/256,667, filed on Oct. 30, 2009.

(30) Foreign Application Priority Data

Sep. 2, 2009    (IN) .................... 2008/MUM/2009

(51) Int. Cl.
| A61K 31/047 | (2006.01) |
| A61P 27/02 | (2006.01) |
| A61K 36/28 | (2006.01) |

(52) U.S. Cl.
CPC .................... A61K 36/28 (2013.01)

(58) Field of Classification Search
CPC .................... A61K 31/047; A61P 27/02
See application file for complete search history.

(56) References Cited

U.S. PATENT DOCUMENTS

| 5,308,759 A | 5/1994 | Gierhart |
| 5,382,714 A | 1/1995 | Khachik |
| 5,427,783 A | 6/1995 | Gierhart |
| 5,523,494 A | 6/1996 | Torres-Cardona et al. |
| 5,747,544 A | 5/1998 | Garnett et al. |
| 5,780,693 A | 7/1998 | Bernhard et al. |
| 5,827,652 A | 10/1998 | Garnett et al. |
| 5,854,015 A | 12/1998 | Garnett et al. |
| 5,973,211 A | 10/1999 | Rodriguez |
| 6,075,058 A | 6/2000 | Handelman |
| 6,218,436 B1 | 4/2001 | Howard et al. |
| 6,329,432 B2 | 12/2001 | Howard et al. |
| 6,376,722 B1 | 4/2002 | Sanz et al. |
| 6,504,067 B1 | 1/2003 | Montoya-Olvera et al. |
| RE38,009 E | 2/2003 | Garnett et al. |
| 6,737,535 B2 | 5/2004 | Kumar |
| 6,743,953 B2 | 6/2004 | Kumar et al. |
| 6,743,954 B2 | 6/2004 | Ernst et al. |
| 6,811,801 B2 | 11/2004 | Nguyen et al. |
| 6,936,279 B2 | 8/2005 | Guerra-Santos et al. |
| 7,253,294 B2 | 8/2007 | Hoffman et al. |
| 7,267,830 B2 | 9/2007 | Lang |
| 7,351,424 B2 | 4/2008 | Ornelas-Cravioto et al. |
| RE40,912 E | 9/2009 | Khachik |
| RE40,931 E | 10/2009 | Khachik |
| RE40,938 E | 10/2009 | Khachik |
| 7,622,599 B2 | 11/2009 | Swaminathan et al. |
| 2003/0108598 A1 | 6/2003 | Garnett et al. |
| 2004/0044085 A1 | 3/2004 | Kumar et al. |
| 2004/0081628 A1 | 4/2004 | Gierhart et al. |
| 2005/0147648 A1 | 7/2005 | Gierhart |
| 2005/0171212 A1 | 8/2005 | Gierhart |
| 2006/0089411 A1 | 4/2006 | Gierhart |
| 2007/0032683 A1 | 2/2007 | Xu et al. |
| 2007/0065487 A1 | 3/2007 | Cravioto |
| 2007/0082066 A1 | 4/2007 | Gierhart et al. |
| 2007/0265351 A1 | 11/2007 | Kumar et al. |
| 2008/0051591 A1 | 2/2008 | Swaminathan et al. |
| 2009/0118379 A1 | 5/2009 | Eidenberger |
| 2010/0081850 A1 | 4/2010 | Swaminathan et al. |

FOREIGN PATENT DOCUMENTS

| EP | 0 831 797 | 12/1996 |
| EP | 0 774 251 | 5/1997 |
| WO | 96/40092 | 12/1996 |
| WO | 2009/019712 | 2/2009 |

OTHER PUBLICATIONS

Raju et al., Food Chemistry, vol. 101, issue 4, 2007.*
Sajilata et al., The Carotenoid Pigment Zeaxanthin—A Review (Comprehensive reviews in Food Science and Food Safety), 2008.*
Bone, et al., "Distribution of Macular Pigment Components, Zeaxanthin and Lutein, in Human Retina", Methods in Enzymology, vol. 213, 1992, pp. 360-366.
Snodderly, et al., "Evidence for protection against age-related macular degeneration by carotenoids and antioxidant vitamins", Am J Clin Nutr, vol. 62 (suppl), 1995, pp. 1448S-1461S.
Bone, et al., "Lutein and Zeaxanthin in the Eyes, Serum and Diet of Human Subjects", Exp. Eye Res., vol. 71, 2001, pp. 239-245.
The Eye Diseases Prevalence Research Group, "Prevalence of Age-Related Macular Degeneration in the United States", Arch Ophthalmol, vol. 122, 2004, pp. 564-572.
Seddon, et al., "Dietary Carotenoids, Vitamins A, C, and E, and Advanced Age-Related Macular Degeneration", JAMA, vol. 272, No. 18, 1994, pp. 1413-1420.
Goldbohm, et al., "The Contribution of Various Foods to Intake of Vitamin A and Carotenoids in the Netherlands", Internat. J. Vit. Nutr. Res. vol. 68, 1998, pp. 378-383.

(Continued)

*Primary Examiner* — Zohreh A Fay
(74) *Attorney, Agent, or Firm* — Hamre, Schumann, Mueller & Larson, P.C.

(57) ABSTRACT

A xanthophyll composition that contains macular pigments including trans-lutein and zeaxanthin isomers, namely, (R,R)-zeaxanthin and (R,S)-zeaxanthin, derived from the plant extract/oleoresin containing xanthophylls/xanthophylls esters which is safe for human consumption and useful for nutrition and health care. The composition has at least 80% by weight that is total xanthophylls, of which the ratio of trans-lutein and zeaxanthin isomers being in the range of about 4:1 to about 6:1 and the ratio of the isomers of zeaxanthin being in the range of about 80 to 20:20 to 80.

12 Claims, No Drawings

(56) References Cited

OTHER PUBLICATIONS

Mares-Perlman, et al., "Lutein and Zeaxanthin in the Diet and Serum and Their Relation to Age-related Maculopathy in the Third National Health and Nutrition Examination Survey", American Journal of Epidemoiology, vol. 153, No. 5, 2001, pp. 424-432.
USDA, "References for USDA-NCC Carotenoid Databese for U.S. Foods", 1998, 11 pages.
Sommerberg, et al., "Fruits and vegetables that are sources for lutein and zeaxanthin: the macular pigment in human eyes", Br J Ophthalmol, vol. 82, 1998, pp. 907-910.
Johnson, et al., "Nutritional Manipulation of Primate Retinas, III: Effects of Lutein or Zeaxanthin Supplementation on Adipose Tissue and Retina of Xanthophyll-Free Monkeys", Investigative Ophthalmology & Visual Science, vol. 46, No. 2, Feb. 2005, pp. 692-702.
Bone, et al., "Preliminary Identification of the Human Macular Pigment", Vision Res., vol. 25, No. 11, 1985, pp. 1531-1535.
Bone, et al., "Lutein and Zeaxanthin Dietary Supplements Raise Macular Pigment Density and Serum Concentrations of these Carotenoids in Humans", The Journal of Nutrition, 2003, pp. 992-998.
Bone, et al., "Macular Pigment and Serum Response to Dietary Supplementation with Meso-Zeaxanthin", Invest Ophthalmol Vis Sci, vol. 44: E-Abstract 405, 2003, 2 pages.
Bone, et al., "Distribution of Lutein and Zeaxanthin Stereoisomers in the Human Retina", Exp. Eye Res., vol. 64, 1997, pp. 211-218.
Schiedt, et al., "Absorption, retention and metabolic transformations of carotenoids in rainbow trout, salmon and chicken", Pure & Appl. Chem., vol. 57, No. 5, 1985, pp. 685-692.
Bone, et al., "Stereochemistry of the Human Macular Carotenoids", Investigative Ophthalmology & Visual Science, vol. 34, No. 6, May 1993, pp. 2033-2040.
Mayer, "Reflections on carotenoid synthesis", Pure & Appl. Chem, vol. 66, No. 5, 1994.
Malinow, et al., "Diet-related macular anomalies in monkeys", Invest. Ophthalmol. Vis. Sci., vol. 19, No. 8, 1980, pp. 857-863.
Lundrum, et al., "Lutein, Zeaxanthin, and the Macular Pigment", Archives of Biochemistry and Biophysics, vol. 385, No. 1, Jan. 2001, pp. 28-40.
Chew, et al., "Lutein", Encyclopedia of Dietary Supplements, Feb. 2005, 2 pages.
Arai, et al., "The first isolation of enantiomeric and meso-zeaxanthin in nature", Comp Biochem Physiol B. vol. 83, No. 1, 1986, pp. 121-124—Abstract.
Thurnham, et al., "A supplementation study in human subjects with a combination of meso-zeaxanthin, (3R,3'R)-zeaxanthin and (3R,3'R 6'R)-lutein", British Journal of Nutrition, vol. 100, 2008, pp. 1307-1317.
Bone, et al., "Macular pigment response to a supplement containing meso-zeaxanthin, lutein and zeaxanthin", Nutrition & Metabolism, vol. 4, No. 12, 2007, 8 pages.
Thurnham, "Macular zeaxanthins and lutein—a review of dietary sources and bioavailability and some relationships with macular pigment optical density and age-related macular disease", Nutrition Research Reviews, No. 20, 2007, pp. 163-179.
Schlatterer, et al., "Quantification of 3R, 3'R-zeaxanthin in plant derived food by a diastereomeric dilution assay applying chiral high-performance liquid chromatography", Journal of Chromatography A, vol. 1137, No. 2, Dec. 2006, pp. 216-222—Abstract.
Andrewes, "Isomerization of ε-Carotene to β-Carotene and of Lutein to Zeaxanthin", Acta Chem. Scand. B, vol. 28, No. 1, 1974, pp. 137-138.
Kruger, et al., "An innovative approach to the determination of safety for dietary ingredient derived from a new source: case study using a crystalline lutein product", Food and Chemical Toxicology, vol. 40, No. 11, Nov. 2002, pp. 1535-1549—Abstract.
Chang, "Thirteen-Week Oral (Gavage) Toxicity of Mesozeaxanthin in Han Wistar Rats with a 4-Week Recovery" Gene Logic, Study No. 1567-04370, 2006, 26 pages.
Thürmann, et al., "Plasma kinetics of lutein, zeaxanthin, and 3'-dehydro-lutein after multiple oral doses of a lutein supplement", Am J Clin Nutr, vol. 82, 2005, pp. 88-97.
Nebeling, et al., "Changes in Carotenoid Intake in the United States: The 1987 and 1992 National Health Interview Surveys", Journal of the American Dietetic Association, vol. 97, No. 9, 1997, pp. 991-996—Abstract.
Le Marchand, et al., "An ecological study of diet and lung cancer in the South Pacific", International Journal of Cancer, vol. 63, No. 1, Sep. 1995, pp. 18-23, Abstract.
Ernst, Hansgeorg, "Recent advances in industrial carotenoid synthesis", Pure Appl. Chem., vol. 74, on. 11, pp. 2213-2226, 2002.
Gau et al., "Mass spectrometric identification of xanthophyll fatty acid esters from marigold flowers (*Tagetes erecta*) obtained by high performances liquid chromatography and Craig counter-current distribution", Journal of Chromatography, vol. 262, pp. 277-284, 1983.
Communication of a Notice of Opposition, issued in the European Patent No. 2473065, dated Jan. 20, 2017, 21 pages.
Brief EPO Communication, issued in the European Patent No. 2473065, dated Jun. 16, 2017, in response to Letter from the Opponent (filed Jun. 9, 2017), 4 pages.
Shiedt et al., "Carotenoids vol. 1A Isolation and Analysis", Birkhauser Verlag Basel, Chapter 5, pp. 81-108, 1995, (see the above Brief EPO Communication, issued in the European Patent No. 2473065).
Kohler, "Carotenoids vol. 1B Electronic Structure of Carotenoids", Birkhauser Verlag Basel, Chapter 1, pp. 1-12, 1995, (see the above Brief EPO Communication, issued in the European Patent No. 2473065).
Mayer et al., "Carotenoids vol. 2 Synthesis", Birkhauser Verlag Basel, pp. 20-22 and 96-97, 1996, (see the above Brief EPO Communication, issued in the European Patent No. 2473065).
Liaan-Jensen et al., "Carotenoids vol. 4 Natural Function", Birkhauser Verlag Basel, Chapters 3, 7, pp. 24-34, 2008, (see the above Brief EPO Communication, issued in the European Patent No. 2473065).
Khachik, "Carotenoids Nutrition and Health", Birkhauser Verlag Basel, vol. 5, Chapters 2 and 3, pp. 10 and 60-62, 2009, (see the above Brief EPO Communication, issued in the European Patent No. 2473065).

\* cited by examiner

XANTHOPHYLL COMPOSITION CONTAINING MACULAR PIGMENTS AND A PROCESS FOR ITS PREPARATION

FIELD OF THE INVENTION

The present invention relates to a xanthophyll composition containing macular pigments and a process for its preparation. The invention particularly relates to a xanthophyll composition containing macular pigments consisting of trans-lutein and zeaxanthin isomers and a process for its preparation. This invention more particularly relates to a xanthophyll composition containing macular pigments consisting of trans-lutein, zeaxanthin isomers, namely (R,R)-zeaxanthin and (R,S)-zeaxanthin derived from the plant extract/oleoresin containing xanthophylls/xanthophylls esters which is safe for human consumption and useful for nutrition and health applications. More particularly the present invention relates to a xanthophyll composition containing at least 80% by weight of total xanthophylls, of which the trans-lutein content is at least 80% and the remaining being zeaxanthin isomers, namely (R,R)-zeaxanthin and (R,S)-zeaxanthin derived from the plant extracts/oleoresin containing xanthophylls/xanthophylls esters which is safe for human consumption and useful for nutrition and health applications.

The xanthophyll composition of the present invention is useful as an ingredient in nutrition and health applications, as an additive and/or colorant for food and feed applications.

BACKGROUND OF THE INVENTION

The macula is in the center of the retina, directly behind the lens in the eye. It is a tiny area with an yellow color consisting of xanthophylls like lutein, (R,R)-zeaxanthin and (R,S)-zeaxanthin and hence called macular xanthophylls. These act as antioxidants protecting the retina from oxidative degradation and help in sharp vision needed to read, write, drive and see objects clearly. A life time slow and steady damage of the macula can lead to age related macular degeneration (AMD) and cataract. The macular xanthophylls in the diet or supplementation can help in maintaining healthy eyes. Lutein and (R,R)-zeaxanthin can be derived from fruits and vegetables while (R,S)-zeaxanthin from sea foods or dietary supplements or from bio conversion of lutein within the body. Of the various classes of the pigments, the carotenoids are among the most widely distributed in nature with red, yellow and orange color having varied functions like light harvesting and protection against destructive photo-oxidation in terrestrial plants.

Although specific carotenoids have been identified in various fruits and vegetables, bird feathers, egg-yolk, poultry skin, crustaceans and macular eye region, they are especially abundant in marigold petals, corn and leafy vegetables. The correlation between dietary carotenoids and carotenoids found in human serum and plasma indicate that only selected groups of carotenoids make their entry into the human blood stream to exert their effect. Each carotenoid shows an individual pattern of absorption, plasma transport and metabolism.

Carotenoids absorb light in the 400-500 nm region of the visible spectrum. This physical property imparts the characteristic yellow/red colour to the pigments. Carotenoids contain a conjugated backbone composed of isoprene units, which are usually inverted at the center of the molecule, imparting symmetry. Changes in geometrical configuration about the double bonds result in the existence of many cis- and trans-isomers. Mammalian species do not synthesize carotenoids and therefore these have to be obtained from dietary sources such as fruits, vegetables and egg yolks. In the recent years, carotenoids have been reported to have several health benefits, which include prevention and or protection against serious health disorders.

Carotenoids are non-polar compounds classified into two sub-classes, namely, polar compounds called xanthophylls or oxy-carotenoids and non-polar hydrocarbon carotenes like beta-carotene, lycopene, etc. Both the sub-classes have at least nine conjugated double bonds responsible for the characteristic colors of the carotenoids. Xanthophylls have ring structures at the end of the conjugated double bond chain with polar functions like hydroxyl or keto group. The examples for xanthophylls include lutein, zeaxanthin, capsanthin, canthaxanthin, beta-cryptoxanthin, astaxanthin, etc. As natural colorants and also for their role in human health, xanthophylls like lutein, (R,R)-zeaxanthin and (R,S)-zeaxanthin have attracted the renewed attention of scientists and researchers in the biomedical, chemical and nutritional field in recent years.

Lutein and zeaxanthin contribute to yellow and orange-yellow colors respectively. Lutein and zeaxanthin can be present in plant material in the free form and also in ester form. Lutein is present in green leafy vegetables like spinach, kale and broccoli in the free form; fruits like mango, orange and papaya; red paprika, algae, yellow corn, contain lutein in the form of its esters. It is also present in the blood stream and various tissues in human body and particularly in the macula, lens and retina of the eye.

Lutein is chemically designated as beta-ε-carotene 3,3'-diol. Zeaxanthin is formed by the addition of two hydroxy groups to beta-carotene. Since the hydroxy positions are in 3 and 3'-, the chemical name for zeaxanthin is beta, beta-carotene-3,3'-diol. The common name of zeaxanthin is derived from *Zea mays* because this carotenoid was first identified in corn (*Zea mays*).

It can be seen below that lutein is not symmetrical as the position of double bond in the left ring is not identical with the double bond position in the right ring. Zeaxanthin is completely symmetrical with regards to left and right rings due to an extra conjugated double bond compared to lutein.

Xanthophylls can show both optical (R- and S-stereo isomers) and geometrical isomers (trans, E- and cis, Z-). The conformation of R- and S-stereo isomers is based on CD spectral and chiral column HPLC studies while the conformation of cis- and trans-isomers is based on electronic, infrared, NMR, HPLC-MS and HPLC-NMR on-line spectroscopy studies. It is well known that when an organic molecule has a carbon atom with four different types of atoms or groups attached to it, that carbon atom is designated as chiral carbon atom. The chiral carbon atom is responsible for two different spatial arrangements leading to the formation of optical isomers while the number of double bonds of the polyene chain and the presence of a methyl group and the absence of steric hindrance decide the number of trans- and cis-isomers. In the case of trans-zeaxanthin, the carbon atoms at 3 and 3' positions in the two end rings are both chiral atoms.

Thus, trans-zeaxanthin has two chiral centers at the carbon atoms C3 and C3', based on the positions of the secondary hydroxy groups attached to them. Therefore, there are four possible stereo isomers of trans-zeaxanthin namely, (3R-3'R)-isomer, (3S-3'S)-isomer and (3R-3'S)- or (3S-3'R)-isomer. In these isomers (3R-3'S)- and (3S-3'R)- are identical. Thus, there are three chiral isomers of trans-zeaxanthin. The isomer causing rotation of polarized light in a right handed manner is called R-stereo isomer, the isomer causing left handed rotation. S-stereo isomer and the third isomer possessing a two fold opposite effects (R,S; optically inactive) which is called meso-form of zeaxanthin. The structural formulae of lutein, (R,R)-zeaxanthin and (R,S)-meso zeaxanthin are given below.

Billsten et al., Photophysical Properties of Xanthophylls in Carotene Proteins from Human Retina, Photochemistry and Photobiology, 78, 138-145, 2003). At the center of the retinal fovea, zeaxanthin is 50:50 mixture of (trans-3R,3'R)-zeaxanthin and (trans-3R,3'S)-zeaxanthin along with small quantity of (3S,3'S)-zeaxanthin (J. T. Landrum and R. A.

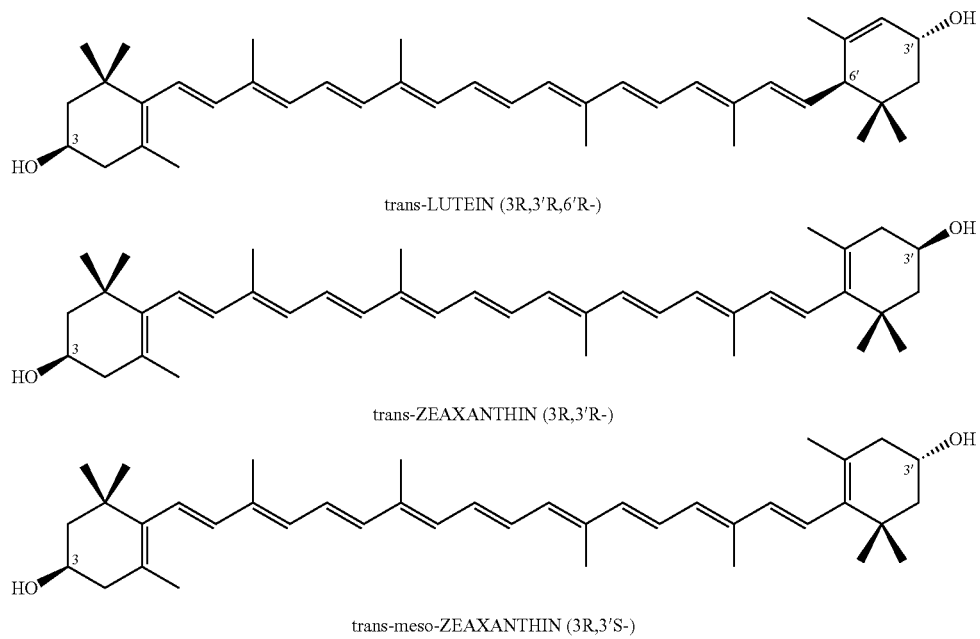

Chemical Structures of Macular Xanthophylls

The conjugated double bonds of lutein and zeaxanthin contribute to the distinctive colors of each pigment, and also influence the ability of these to quench singlet oxygen. Due to the extra conjugated double bond, zeaxanthin is believed to be a stronger anti-oxidant compared to lutein.

The macular pigment of the eye is composed primarily of three xanthophyll pigments (or macular xanthophylls), namely (3R,3'R,6'R)-lutein, (3R,3'R)-zeaxanthin and (3R, 3'S)-zeaxanthin in the order 36, 18 and 18% of the total carotenoid content of the retina along with the remaining 20% consisting of minor carotenoids like oxo-lutein, epi-lutein and ε-,-ε-carotene 3,3'-dione (J. T. Landrum and R. A. Bone, Lutein, Zeaxanthin and the Macular Pigment, Arch. Biochem. Biophys., 385, 28-40, 2001).

Although these xanthophyll pigments are found throughout the tissues of the eye, the highest concentration is seen in the macula lutea region of the retina, including a central depression in the retina called fovea. The concentration of xanthophyll pigments increases progressively towards the center of the macula and in the fovea, the concentration of these xanthophyll pigments are approximately thousand fold higher than in other human tissues. (Landrum et al., Analysis of Zeaxanthin Distribution within Individual Human Retinas, Methods in Enzymology, L. Packer (editor) 213A, 457-467, Academic Press 1992). The fovea is a relatively small area within the macula, in which the cone photoreceptors reach their maximal concentration. About 50% of the total amounts of the xanthophylls are concentrated in the macula where zeaxanthin dominates over lutein by ratio of 2:1 (Handelman et al., Measurements of Carotenoids in Human and Monkey Retinas, in Methods in Enzymology, L. Packer (editor) 213A, 220-230, Academic Press, NY, 1992;

Bone, Lutein, Zeaxanthin and The Macular Pigment, Arch. Biochem., Biophy., 385, 28-40, 2001).

The fovea is particularly important for proper visual function (eg, acuity) disease and damage to this area is known to result in legal blindness. For example, age-related macular degeneration (AMD) is characterized by pathological changes in the retina, retinal pigment epithelium (RPE) and/or the choroids and preferentially affects the macular region of the retina. This is the leading cause of irreversible vision loss in the United States among those more than 65 years old and there is no established treatment available for most patients. The loss of central vision results in the possible inability to recognize faces, to read or write or drive a car and therefore has a significant effect on an individual's ability to live independently. There is ample epidemiological evidence which supports a role for dietary intake of lutein and zeaxanthin in different isomeric forms in protection against age-related cataract and macular degeneration. The detection of oxidation products of lutein and zeaxanthin in the human retina supports the hypothesis that dietary lutein and zeaxanthin may act as antioxidants in the macular region. (Khachik et al., Identification of Lutein and Zeaxanthin Oxidation Products in Human and Monkey Retinas, Invest. Opthalmol. and Vis. Sci., 38, 1802-1811, 1997)

Of the 40 to 50 carotenoids typically consumed in the human diet, lutein and zeaxanthin, are deposited at an up to 5 fold higher content in the macular region of the retina as compared to the peripheral retina. Zeaxanthin is preferentially accumulated in the foveal region, whereas lutein is abundant in the perifoveal region.

Regarding the location of xanthophylls at a cellular level, they are reported to be bound to specific proteins referred to as xanthophylls binding protein (XBP). The XBP is suggested to be involved in the uptake of lutein and zeaxanthin from the blood stream and stabilization of the same in the retina. The study of xanthophylls and XBP by femto-second transient absorption spectroscopy showed better stability for (3R,3'S)-zeaxanthin enriched XBP compared to (3R,3'R)-zeaxanthin while the photo physical properties of the xanthophylls: (3R,3'R)-zeaxanthin and (3R,3'S,meso)-zeaxanthin are generally identical. It is likely that the meso-zeaxanthin is better accommodated with XBP wherein the protein protects the xanthophylls from degradation by free radicals. Thus, the complex may be a better antioxidant than the free xanthophylls, facilitating improved protection of ocular tissue from oxidative damages. (Billsten et al., Photophysical Properties of Xanthophylls in Caroteno proteins from Human Retina, Photochemistry and Photobiology, 78, 138-145, 2003)

Several functions have been attributed to macular pigments including the reduction of the damaging effects of photo-oxidation from blue light absorbed by the eye, reduction of the effects of light scatter and chromatic aberration on visual performance, and protection against the adverse effects of photochemical reactions because of the antioxidant properties of the carotenoids.

The ability to increase the amount of macular pigment by dietary supplementation with lutein has been demonstrated (Landrum et al., Dietary Lutein Supplementation Increases Macular Pigment, FASEB. J, 10, A242, 1996). The reduced vision function due to cataract and the adult blindness due to AMD can be substantially controlled by consuming fruits and vegetables and dietary supplements containing lutein and (R,R)-zeaxanthin and (R,S)-zeaxanthin available from sea foods denying the vegetarian population. Although (R,S)-zeaxanthin present in eye is considered a metabolic product originating from lutein, the need for dietary supplementation of (R,S)-zeaxanthin is now recognized to improve the macular pigment density. (Landrum and Bone, Functional Foods and Nutraceuticals, 1 Sep. 2001). Similarly, the study has shown that (R,R)-zeaxanthin gains entry to blood and finally to macula. (Breithaupt et al., Comparison of Plasma Responses in Human subjects after the Ingestion of (3R,3'R)-zeaxanthin Dipalmitate from Wolfberry (*Lycium barbarum*) and Non-esterified (3R,3'R)-zeaxanthin using Chiral HPLC, Brit. J. Nutr. 91, 707-713, 2004). Lutein and zeaxanthin dietary supplements in human trials have shown to raise the macular pigment density and serum concentrations of these carotenoids (Bone et. al., Lutein and Zeaxanthin Dietary Supplements Raise Macular Pigment Density and Serum Concentrations of These Carotenoids in Humans, J. Nutr., 133, 992-998, 2003).

Dietary Sources of Lutein and Zeaxanthin

Lutein is a common carotenoid found in most fruits and vegetables, while zeaxanthin in the (R,R)-isomer form is present only in minute quantities in most fruits and vegetables. Dietary sources of zeaxanthin are limited to greens, certain yellow/orange fruits and vegetables such as corn, nectarines, oranges, papaya, persimmons and squash. Capsicum annum is another most common spice widely used which is a good source of zeaxanthin. Wolfberry (*Lycium barbarum*), fructus lycii or Gou Qi Zi plant has small red berries which are commonly used in Chinese home cooking and has been shown to have a high content of zeaxanthin (mainly as zeaxanthin dipalmitate) but negligible amounts of lutein. The dried fruit of wolfberry is prescribed by Chinese herbalists as a therapeutic agent for a number of eye diseases. In France, lutein dipalmitate (Helenien) isolated from the blossom leafs of *Helenium autumnale* is reported to be used for the treatment of the visual disorders. (Wolfgang Gau, Hans-Jurgen Ploschke and Christian Wunsche, Mass Spectrometric Identification of Xanthophylls Fatty Acid Esters From Marigold Flowers (*Tagetes erecta*) Obtained by HPLC and Craig Counter Current Distribution, J. Chrom. 262,277-284, 1983)

As already mentioned earlier, the dietary source of meso-zeaxanthin is mainly from seafoods like shrimps, fish, turtle, etc, thereby the vegetarian population is deprived of meso-zeaxanthin. However, there is a patent available for pharmaceutical composition containing meso-zeaxanthin for the treatment of retinal disorders like increasing the deposition of macular pigments in the human eye and therapeutic treatment or prophylaxis of AMD (Howard et al., Meso-zeaxanthin Formulations for Treatment of Retinal Disorders, U.S. Pat. No. 6,329,432, 2001).

Lutein and zeaxanthin occur naturally in trans-isomeric form in fruits, vegetables and flowers (marigold). Because of processing conditions due to heat and light, a small percentage of trans- is converted into cis-isomeric form. Therefore, the preferred bio-available form is trans-isomeric as evidenced from the data of geometric isomers compositional analysis of human plasma. (Khachik et al., Isolation and Structure Elucidation of Geometric Isomers of Lutein, Zeaxanthin in Extracts of Human Plasma, J. Chrom. 582, 153-156, 1992). In view of this, it is desirable to use the trans-isomeric form of lutein and zeaxanthin as (R,R)-, (R,S)- in dietary supplements.

To date, little is known about the mechanism of formation, uptake and deposition of meso-zeaxanthin in the retina of the eye. Khachik et al. have reported the presence of 2-3% of (3R,3'S,meso)-zeaxanthin in twenty normal human plasma samples and proposed the metabolic pathways of its formation from dietary lutein and zeaxanthin. It is not clear whether the deposition of meso-zeaxanthin in the retina routes through serum or are produced from lutein/zeaxanthin within the retina. (Khachik et al., in a chapter on Dietary carotenoids and their metabolites as potentially useful chemo protective agents against cancer, in "Antioxidant food supplement in human health, Eds. Packer et al., Academic Press London, page 203-29, 1999). However, Breithaupt et al. did not find the presence of meso-zeaxanthin in human plasma obtained 24 hrs after ingestion of (3R,3'R)-zeaxanthin (ester or free form) in a single blind cross over study using two groups each consisting of six volunteers. The chiral LC-ApcI-MS was used for detection in the pooled plasma sample. (Breithaupt et al., Comparison of plasma responses in human subjects after the ingestion of 3R,3'R-zeaxanthin Dipalmitate from Wolfberry (*Lycium barbarum*) and Non-esterified 3R,3'R-zeaxanthin using Chiral HPLC, Brit. J. Nutr. 91, 707-713, 2004).

There is evidence and reasons supporting the hypothesis that the carotenoids lutein, zeaxanthin and meso-zeaxanthin are readily bio-available and consequently increase macular pigment levels (Landrum and Bone, Meso-zeaxanthin—A Cutting Edge Carotenoid, Functional Foods and Nutraceuticals, 10 Sep. 2001; Bone et al. Macular Pigment Response to a Supplement Containing Meso-zeaxanthin, Nutr. Metabol. 11.1-8 (2007); Bone et al., Macular Pigment Response to a Xanthophyll Supplement of Lutein, Zeaxanthin and Meso-zeaxanthin. Proc. Nutr. Soc., 105A, (2006); Thurnham et al., Macular Zeaxanthin and Lutein—a Review of Dietary Sources and Bio-availability and Some Relationship with Macular Pigment Optical Density and Age-related Macular Disease, Nutr. Res. Reviews, 20, 163-179 (2007); Thurnham et al., A Supplementation Study in Human Subjects with a Combination of meso-zeaxanthin, (3R,3'R)-Zeaxanthin and (3R,3'R,6'R)-Lutein, Brit. J. Nutr. 99, 1-8, 2008); E. E. Connolly et al., Augmentation of macular pigment following supplementation with all three carotenoids: An exploratory study" Current Eye Res., 35, 335-351 (2010).

In present days, there is high demand for xanthophyll crystals containing high amounts of trans-lutein and/or zeaxanthin for its use as antioxidants, prevention of cataract and macular degeneration, as lung cancer-preventive agent, as agents for the absorption of harmful ultra-violet light from sun rays and quencher of photo-induced free radical and reactive oxygen species, etc. A number of commercial products from natural source are now available to facilitate the formulation of industrial and commercial products with lutein or (R,R)-zeaxanthin. However, to our knowledge xanthophyll composition containing all the essential macular xanthophylls and high concentrations of particularly trans-lutein at least 85% and balance comprising of (R,R)-zeaxanthin and (R,S)-zeaxanthin in equal or higher ratios derived from the same natural source (marigold flower petals) as commercial lutein or zeaxanthin are not available. Evidence of the protective role of trans-lutein, (R,R)-zeaxanthin and (R,S)-zeaxanthin in maintaining eye health has been found based on correlation between dietary supplements vs serum levels and the macular pigment density (Bone et al, Macular Pigment Response to a Supplement Containing Meso-zeaxanthin, Lutein and Zeaxanthin, Nutr. Metabol. 11.1-8 (2007); Bone et al., Macular Pigment Response to a Xanthophyll Supplement of Lutein, Zeaxanthin and Meso-zeaxanthin. Proc. Nutr. Soc., 105A, (2006); Thurnham et al., A Supplementation Study in Human Subjects with a Combination of Meso-zeaxanthin, (3R,3'R)-zeaxanthin and (3R,3'R,6'R)lutein, Brit. J. Nutr. 99, 1-8 (2008).

PRIOR ART

The macular pigment of the eye is composed chiefly of lutein, (R,R)-zeaxanthin and (R,S)-zeaxanthin in the approximate ratio of 2:1:1 in the retina. These pigments represent 72% of the total carotenoids in the eye and the balance being other carotenoids (Landrum and Bone, Lutein Zeaxanthin and the Macular Pigments, Arch. Biochem. Biophys. 385, 28-40, 2001). The predominant xanthophylls pigment in the diet is lutein and comes from fruits and vegetables. The average intake of lutein in the USA is between 1-3 mg per day which includes about 10-20% (R,R)-zeaxanthin (E. Y. Chew and San Gio Vanni, "Lutein" in Encyclopedia of Dietary Supplements, page 409-420, 2005 published by Marcel Dekker). (R,S)-zeaxanthin is not found in normal diet but present in certain sea foods like shrimp, fish and turtle. (Maoka et. al., The First Isolation of Enantiomeric and Meso-zeaxanthin in Nature. Comp. Biochem. Physiol., 83B, 121-124, 1986). In the recent years, substantial amounts of zeaxanthin, namely (R,R)- and (R,S)-zeaxanthin, are reported to be present in the chicken egg yolks in Mexico originating from chicken feeds containing both (R,R)- and (R,S)-zeaxanthin. (Thurnham et. al, A Supplementation Study in Human Subjects with a Combination of Meso-zeaxanthin, (3R,3'R)-zeaxanthin and (3R, 3'R,6'R)-lutein, Brit. J. Nutr. 99, 1-8 (2008)). During the last 5 years, dietary supplements containing (R,S)-zeaxanthin are available in US markets sold under the brand names "Lutein Plus" and "LMZ3" and in Europe as "Lutein Plus" and "Macushield"

In addition, there are pharmaceutical formulations containing (R,S)-zeaxanthin for increasing macular pigment density in the human eye and for therapeutic treatment or prophylaxis of diseases and disorders of macula. (Howard et. al., Meso-zeaxanthin Formulations for Treatment of Retinal Disorders, U.S. Pat. No. 6,379,432, 2001). The dietary lutein supplements chiefly contain lutein 80-90% and low amounts of zeaxanthin and total absence of (R,S)-zeaxanthin. The xanthophyll composition of blended samples—namely Lutein Plus; lutein 50%, (R,R)-zeaxanthin 13% and (R,S)-zeaxanthin 37%; lutein 54%, (R,R)-zeaxanthin 6% and (R,S)-zeaxanthin 40% (Thurnham et al, A Supplementation Study in Human Subjects with a Combination of Meso-Zeaxanthin, (R,R)-zeaxanthin and Lutein, Brit. J. Nutr. 99, 1-8 (2008); Quantum Nutritionals, MI 48390, USA; Lutein 25%, (R,R)-zeaxanthin 6% and (R,S)-zeaxanthin 68%; Bone et al., Macular Pigment Response to a Supplement Containing Meso-zeaxanthin, Lutein and Zeaxanthin, Nutri. Metabol 4, 12, 2007); Meso-zeaxanthin Concentrate, lutein 5%, (R,R)-zeaxanthin 5% and (R,S)-zeaxanthin 85%; yolk lyophilised from chicken eggs lutein 34%, (R,R)-zeaxanthin 12.80% and (R,S)-zeaxanthin 7.20% and other carotenoids (Thurnham, Macular Zeaxanthin and Lutein—A Review of Dietary Sources and Bio-availability and Some Relations with MPOD and ARMD, Nutri. Res. reviews 20, 163-179, 2007). Pure (R,S)-zeaxanthin more than 99% purity (Schiatterer et al., Quantification of (3R, 3'R)-zeaxanthin in Plant Derived Food by diastereoisomeric dilution assay applying Chiral HPLC, J. Chromatography A, 1137, 216-222, 2006); (R,S)-zeaxanthin (synthetic) 99% (Ernst et al., U.S. Pat. No. 6,743,954, 2004); xanthophyll composition lutein 3.53% (R,R)-zeaxanthin 5.77% and (R,S)-zeaxanthin 90.57% (Kumar et al., US Patent Application Publication No. 2007/0265351). Recently, a combination of dietary supplements cobeadlet formulation consisting of lutein 2 mg, zeaxanthin 0.5 mg and (R,S)-zeaxanthin 0.5 mg is reported for inhibiting the process of macular degeneration and promoting healthy vision (Lang, Composition and methods for inhibiting the progression of macular degeneration and promoting healthy vision, U.S. Pat. No. 7,267,830, 2007).

As early as in 1946, Karrer and Jucker reported the sodium ethoxide catalyzed isomerization reaction of lutein to zeaxanthin (P. Karrer and E. Jucker, Helv. Chim. Acta, 30, 266, 1947). Later in 1971-72 Buchecker et al. assigned R-chirality to lutein based on PMR analysis and attempts to isomerize lutein to R,R-zeaxanthin failed (Chimia, 25, 192, 1971; ibid, 26, 134, 1972). Andrewes et al. reported the stereochemical aspects of isomerization reaction of (3R,3'R, 6R)-lutein (optically active) which resulted in (3R,3'S)-zeaxanthin which was trans-isomeric and optically inactive based on CD spectral studies (Isomerization of Epsilon-carotene to Beta-carotene and Lutein to Zeaxanthin, Acta Chem. Scand., B28, 139, 1974). The above process results in low yield of 10 to 15% optically inactive (3R,3'S,meso)-zeaxanthin and uses benzene and DMSO which are objectionable for use in food and health supplements.

Rodriguez has described a method of isomerising lutein to yield a mixture of zeaxanthin epimers by employing non aqueous media and heating a mixture of alkali and propylene glycol. Though the circular dichroism spectrum indicated the formation of meso-isomer of zeaxanthin, no attempts were made to quantify the meso-zeaxanthin content and also provide the composition of the isomerised products. (U.S. Pat. No. 5,973,211, 1999). According to our knowledge, hither to food grade xanthophyll composition containing at least 80% by weight of total xanthophylls, higher levels of trans-lutein content (70 to 80%) and the remaining being (R,R)-zeaxanthin and (R,S)-zeaxanthin is not hitherto reported. Such a composition will form an ideal and essential dietary supplements which help in maintaining healthy vision. Further, the composition may be deemed to be safe based on the factors supporting reagents employed in the process and the literature data available regarding the toxicological safety for the similar individual xanthophylls. (Kruger et al., Food & Chem. Toxicol., 40, 1535-1549 (2002); Chang, Thirteen week Toxicity of Meso-zeaxanthin in Han Wister Rats with a Four Week Recovery Gene Logic No. 156704370 (2006).

Humans consume 1 to 3 mg lutein per day and the lutein:zeaxanthin ratio in the diet is about 5:1, (Petra A Thürmann, Wolfgang Schalch, Jean-Claude Aebischer, Ute Tenter and William Cohn, Plasma kinetics of lutein, zeaxanthin, and 3-dehydro-lutein after multiple oral doses of a lutein supplement, American Journal of Clinical Nutrition, Vol. 82, No. 1, 88-97, July 2005; Nebeling L C, Forman M R, Graubard B I, Snyder R A. Changes in carotenoid intake in the United States: the 1987 and 1992 National Health Interview Surveys. J Am Diet Assoc, 991-6.1997; Le Marchand L, Hankin J H, Bach F, et al. An ecological study of diet and lung cancer in the South Pacific. Int J Cancer; 63:18-23, 1995. Mohamedshah F, Douglas J S, Amann M M, Heimbach J M. Dietary intakes of lutein+zeaxanthin and total carotenoids among Americans age 50 and above. FASEB J, 13:A554 (abstr)., 1999)

The plasma lutein:zeaxanthin ratio is 4 or 5:1. (Emily Chew and John Paul SanGiovanni, in Encyclopedia of Dietary Supplements, Ed. Paul Coates, Marcel Dekker, pages 409-421, 2005)

Under the circumstances explained above, it is desirable and useful for industry and nutritional product formulators to have a xanthophyll concentrate consisting of all the macular xanthophylls obtained from a commercially scalable process, and made from natural source material same as that which is already accepted by the market for lutein, (R,R)-zeaxanthin and (R,S)-zeaxanthin. The product prepared should have 5:1 lutein:zeaxanthin ratio, as found in the regular diet and in plasma. The product so prepared should also be made from safe solvents (GRAS) for producing dietary supplements suitable for human consumption, with minimum solvent residues and specifications of lutein and zeaxanthin isomers keeping in mind visual function and market requirements.

OBJECTIVES OF THE PRESENT INVENTION

Therefore, the main objective of the present invention is to provide a xanthophyll composition containing macular pigments consisting of trans-lutein, zeaxanthin isomers, namely (R,R)-zeaxanthin and (R,S)-zeaxanthin derived from the plant extract/oleoresin containing xanthophylls/xanthophylls esters which is safe for human consumption and useful for nutrition and health care.

Another objective of the present invention is to provide a xanthophyll composition containing at least 80% by weight of total xanthophylls of which the trans-lutein content is at least 80% by weight and the remaining being zeaxanthin isomers, namely (R,R)-zeaxanthin and (R,S)-zeaxanthin derived from the plant extract/oleoresin containing xanthophylls/xanthophylls esters which is safe for human consumption and useful for nutrition and health care.

Yet another objective of the present invention is to provide a xanthophyll composition containing at least 85% by weight of total xanthophylls, out of which the trans-lutein content is at least 85% by weight and the remaining being zeaxanthin isomers, namely (R,R)-zeaxanthin and (R,S)-zeaxanthin derived from the plant extract/oleoresin containing xanthophylls/xanthophylls esters which is safe for human consumption and useful for nutrition and health care.

Yet another objective of the present invention is to provide a xanthophyll composition wherein the composition contains at least 85% by weight of total xanthophylls, out of which at least 80% by weight being trans-lutein, at least 6% by weight being (R,R)-zeaxanthin and at least 6% by weight being (R,S)-zeaxanthin derived from the plant extract/oleoresin containing xanthophylls/xanthophylls esters which is safe for human consumption and useful for nutrition and health care.

Still another objective of the present invention is to provide a xanthophyll composition wherein the composition contains at least 85% by weight trans-lutein and at least 4% by weight (R,R)-zeaxanthin and at least 5% by weight (R,S)-zeaxanthin derived from the plant extract/oleoresin containing xanthophylls/xanthophylls esters which is safe for human consumption and useful for nutrition and health care.

Yet another objective of the present invention is to provide a xanthophyll composition wherein the composition contains at least 85% by weight of total xanthophylls, out of which at least 80% by weight being trans-lutein, the remaining 15% by weight being zeaxanthin isomers, namely (R,R)-zeaxanthin and (R,S)-zeaxanthin derived from the plant extract/oleoresin containing xanthophylls/xanthophylls esters which is safe for human consumption and useful for nutrition and health care.

Still another objective of the present invention is to provide a process for the preparation of the xanthophyll composition containing macular pigments consisting of trans-lutein, zeaxanthin isomers, namely (R,R)-zeaxanthin and (R,S)-zeaxanthin derived from the plant extract/oleoresin containing xanthophylls/xanthophylls esters which is safe for human consumption and useful for nutrition and health care The above mentioned objectives have been achieved by the present invention based on our following findings that:

a) The saponification step to convert xanthophyll esters present in plant extract/oleoresin into the de-esterified form can be combined with limited isomerization of lutein to produce xanthophyll composition containing higher amount of trans-lutein, the remaining being zeaxanthin isomers namely, (R,R)-zeaxanthin and (R,S)-zeaxanthin and traces of other carotenoids derived from the plant extract/oleoresin containing xanthophyll/xanthophylls esters which is safe for human consumption and useful for nutrition and health care.

b) in the saponification step, potassium hydroxide or sodium hydroxide can be dissolved in 1-propanol with out the addition of water.

c) the temperature of the saponification/isomerization can be between 70 to 100 Deg C. preferably around at 95 degree and the period of saponification can be 1-2 hrs. and d) the ethyl acetate employed in the process can be recovered and used if required, there by making the process economical.

SUMMARY OF THE INVENTION

Accordingly, the present invention provides a xanthophyll composition containing macular pigments consisting of trans-lutein, zeaxanthin isomers, namely, (R,R)-zeaxanthin and (R,S)-zeaxanthin, derived from the plant extract/oleoresin containing xanthophylls/xanthophylls esters which is safe for human consumption and useful for nutrition and health care which comprises of at least 80% by weight is total xanthophylls, of which the ratio of trans-lutein and zeaxanthin isomers being in the range of 4:1 to 6:1 and the ratio of the isomers of zeaxanthin being in the range of 80 to 20:20 to 80. In some embodiments, the ratio of trans-lutein and zeaxanthin isomers is at a ratio of about 5:1.

According to another embodiment of the present invention there is provided a xanthophyll composition wherein the composition contains at least 85% by weight of total xanthophylls, of which the trans-lutein content is at least 85% and the ratio of trans-lutein and zeaxanthin isomers being in the range of 4:1 to 6:1 and the ratio of the isomers of zeaxanthin being in the range of 80 to 20:20 to 80

According to yet another embodiment of the present invention there is provided a xanthophyll composition wherein the composition contains at least 85% by weight of total xanthophylls, of which at least 80% by weight being trans-lutein, at least 6% by weight being (R,R)-zeaxanthin and at least 6% by weight being (R,S)-zeaxanthin, According to another embodiment of the present invention there is provided a xanthophyll composition wherein the composition contains at least 85% by weight trans-lutein and at least 4% by weight (R,R)-zeaxanthin and at least 5% by weight (R,S)-zeaxanthin.

According to still another embodiment of the present invention there is provided a xanthophyll composition wherein the composition contains at least 85% by weight of total xanthophylls, of which at least 80% by weight being trans-lutein, the remaining 15% by weight being zeaxanthin isomers, namely (R,R)-zeaxanthin and (R,S)-zeaxanthin.

According to further embodiment of the present invention there is provided a process for the preparation of a xanthophyll composition containing macular pigments consisting of trans-lutein, zeaxanthin isomers, namely (R,R)-zeaxanthin and (R,S)-zeaxanthin derived from the plant extract/oleoresin containing xanthophylls/xanthophylls esters which is safe for human consumption and useful for nutrition and health care. which comprises:

(a) saponifying and partially isomerising simultaneously the xanthophyll esters present in the plant extract/oleoresin containing xanthophyll esters by admixing the extract/oleoresin with alkaline solution of 1-propanol, the ratio of alkali and 1-propanol being in the range of 1:0.5 to 1:1 by weight/volume., heating the resultant mass at a temperature in the range 70-100 degree C., preferably 95 Deg C. for a period in the range of 1 to 5 hrs to obtain a saponified/isomerised crude concentrate (b) admixing the resultant saponified/isomerised crude concentrate obtained in step (a) with water, the ratio of the concentrate and water used being in the range from 1:2 to 1:3 volume/volume, to form a diluted oily mixture (c) extracting the diluted oily mixture obtained in step (b) with ethyl acetate, the ratio of diluted oily mixture and ethyl acetate used being in the range of 1:1.5 to 1:2 volume/volume to get an extract containing the xanthophyll composition (d) evaporating the composition obtained in step (c) to remove ethyl acetate (e) purifying the composition resulting from step (d). by washing first with non polar and later with polar solvents and filtering (f) drying the resulting composition under vacuum at a temperature in the range of 40 to 45 Deg C. for a period ranging from 48-72 hours.

(g) if desired recovering the ethyl acetate used in step (c) by conventional methods and if required reused and (h) storing the resulting composition in an inert atmosphere at −20 Deg C.

By adjusting the temperature, period and the amount of alkali in the step (a) the ratios in steps (b) and (c), the desired composition of the present invention can be obtained It is to be noted that the invention envisages the use of leafy and green vegetables corn, fruits and marigolds as the source for the xanthophylls oleoresin. But considering that lutein is present along with zeaxanthin in free form associated with large amounts of chlorophyll and other undesirable carotenoids in most of the fruits, though according to the present invention the use of leafy and green vegetables corn, fruits is possible and considering the low concentration of lutein and zeaxanthin in the above materials and further the elaborate steps of purification which is required being not economical, marigold is the preferred choice as the starting material for the preparation of the composition of the present invention Specifically, commercially available food grade marigold oleoresin produced by hexane extraction can be used as starting material (Kumar et. al Process for the Preparation of Xanthophylls Crystals, U.S. Pat. No. 6,743,953, 2004; Kumar U.S. Pat. No. 6,737,535, 2004) for the preparation of the xanthophyll composition comprising of trans-lutein, and zeaxanthin isomers.

Marigold flower (*Tagetes erecta*) is considered to be the best possible commercial source for trans-lutein as it contains lutein mono- and diesters as the major carotenoid constituents. Marigold extract/oleoresin obtained from the dry flower meal contains around 20-40% lutein esters, depending on the cultivar variety and processes of extraction. In addition to lutein, marigold also contains 5% (R,R)-zeaxanthin and traces of alpha- and beta-cryptoxanthin and beta carotene. (Khachik U.S. Pat. No. 5,382,714, 1995)

The alkali used in step (a) may be selected from sodium hydroxide or potassium hydroxide.

The non-polar solvent used in step (d) may be a hydrocarbon solvent which may be selected from pentane, hexane and heptane, and the like, preferably hexane. The polar solvent used in step (e) may be selected from a lower aliphatic alcohol.

The inert atmosphere used for storing the resulting composition may be maintained inert gas like nitrogen

DETAILED DESCRIPTION OF THE PROCESS

In the present invention the extract containing xanthophyll ester is mixed with 1-propanol in which alkali is already dissolved. The ratio of alkali to 1-propanol and the plant extract is 0.5-1:0.5-1.0 and 1.0 respectively. The mixture is heated to a temperature of 90 degree C. and maintained for 1-5 hours, under agitation. The total xanthophylls in the reaction mixture is determined by Spectrophotometric analysis (AOAC-16th Edition Method 970.64) while the HPLC analysis of the same provides the percentage of trans-lutein and zeaxanthin. (Hadden et al., J. Agric. Food. Chem, 47, 4189-494, 1999).

The saponification of the extract/oleoresin results in the liberation of xanthophylls in free form along with alkali salts of fatty acids. The isomerization reaction converts part of the lutein from marigold into (R,S)-zeaxanthin. The isomerization of lutein to zeaxanthin isomers can be varied by changing process parameters such as alkali:solvent ratio, temperature and duration. The composition of the xanthophylls in the reaction mixture is analyzed by extracting into hexane:acetone:ethanol:toluene (10:7:6:7 v/v) followed by addition of hexane and 10% sodium sulphate solution and analyzing the upper layer by HPLC.

After obtaining the desired degree of isomerization and the xanthophylls composition with trans-lutein content typically around 85%, the reaction mixture is diluted with water and stirred well at room temperature to obtain an yellow oily layer containing xanthophylls in free form associated with fatty acid, soaps and impurities.

After transferring this oily layer into a separatory funnel, ethyl acetate is added and the xanthophylls extracted. The ethyl acetate layer is washed twice with an equal volume of de-ionized water. Thus, the fatty acids and soapy materials are removed into water which is then discarded. The ethyl acetate extract is concentrated by distilling off the solvent under reduced pressure to recover ethyl acetate and the crude xanthophyll concentrate.

The xanthophyll concentrate composition is subjected to purification by agitating with hexane at room temperature for one hour, followed by filtration. The xanthophyll mass is further washed with ethanol and the resulting orange crystals is dried under vacuum at ambient temperature for 72 hours.

The composition of the purified xanthophyll product is shown to consist of approximately 80 to 90% total xanthophylls by weight, by spectrophotometric analysis and the composition of the carotenoids of the xanthophylls 80 to 85% trans-lutein and typically around 15 to 20% zeaxanthin isomers, and sometimes as low as about 11.5%, by HPLC analysis with Cosmosil 5 SL-11-column, 250 4.61 i.d. 5 m, Nacali Tesque co. Ltd. Kyoto, Japan, with acetone:n-hexane (1:9) at a flow rate of 1 mL/min. using a Hitachi L 6200 pump and L-4250 UV-Vis detector set at 450 nm. The chiral HPLC was performed for separation and quantitation of the (R,R)-zeaxanthin and (R,S)-zeaxanthin (collectively referred to herein as zeaxanthin isomers), using Sumichiral OA-2000.

The composition of the present invention contains at least 80% by weight of lutein, which is derived from plant extract/oleoresin containing xanthophylls/xanthophylls esters and its safety has been well established (Kuzhuvelil Bhaskarannair Harikumar et al, Toxicity Profile of Lutein and Lutein Ester Isolated From Marigold Flowers (*Tagetes erecta*), International Journal of Toxicology, Vol. 27, No. 1, 1-9 (2008). The remaining composition consists of (R,R)-zeaxanthin which is extracted along with lutein and its safety is established along with lutein in the above study. The rest of the composition comprises of (R,S)-isomer of zeaxanthin, which is also formed from lutein. Further, the process for preparing the composition of the present invention is carried out under cGMP (current Good Manufacturing Practice) conditions The process is carried out following ISO 22000 guidelines and with food safety being monitored through HACCP (Hazard Analysis and Critical Control Points) as described there under.

Therefore, the composition of the present invention meets all the safety requirements and can be regarded as safe for human consumption. As explained in previous paragraphs, (R,S)-isomer of zeaxanthin is present in macula and is formed by the action of enzymes in the body on lutein.

Therefore, the composition of the present invention comprising of trans-lutein, (R,R)-zeaxanthin and (R,S)-zeaxanthin is safe for human consumption.

The details of the invention are given in the following examples which are provided to illustrate the invention and therefore should not be considered to limit the scope of the present invention.

Example. 1

Marigold oleoresin (100.3 g) containing 135.40 g/kg xanthophyll content (by spectrophotometric method) was mixed with 50 g potassium hydroxide dissolved in 50 ml 1-propanol. The reaction mixture was heated and maintained at 95.degree.C. for a period of 2 hrs. During the reaction stage the sample was taken for analysis of trans-lutein and zeaxanthin content using HPLC. The reaction mass was stirred with 500 ml distilled water at room temperature. The mixture was taken into a separatory funnel and extracted with equal volume of ethyl acetate. This exercise was done 5 times. The ethyl acetate layer was collected and washed with distilled water for removing the excess alkali, soapy materials and other water-soluble impurities. The ethyl acetate layer was distilled off under reduced pressure to get 72.10 g saponified crude extract.

This crude extract (72 g) obtained as described above was subjected to purification by stirring with 360 ml of hexane at room temperature for 1 hr, followed by filtration. 26.20 g wet of a precipitate was obtained which was washed with 262 ml ethanol at room temp for 1 hr followed by filtration. The resulting orange crystals were vacuum dried at ambient temperature for 72 hrs. and stored under nitrogen atmosphere The yield of the xanthophyll composition was 10.40 g having xanthophyll content 83.29% by weight (as determined by UV/Vis spectrophotometry). The composition of the product was trans-lutein 80.80% and zeaxanthin isomers 19.2% determined by HPLC analysis. The Chiral HPLC analysis (Sumichiral OA-2000 Column; solvent n-hexane: chloroform (48:8) showed (R,R)-zeaxanthin 46.3% and R,S)-zeaxanthin 53.7%.

Example: 2

Marigold oleoresin (50 g) containing 124.10 g/kg xanthophyll content (by spectrophotometric method) was mixed with 25 g potassium hydroxide dissolved in 25 ml 1-propanol.) The reaction mixture was heated and maintained at 95.degree.C. for a period of 1 hr. During the reaction stage the sample was taken for analysis of trans-lutein and zeaxanthin content using HPLC. The reaction mass obtained was stirred with 250 ml distilled water at room temperature. The mixture was taken into a separatory funnel and extracted with equal volume of ethyl acetate. This exercise was repeated 5 times. The ethyl acetate layer was collected and washed with distilled water for removing the excess alkali, soapy materials and other water-soluble impurities. The ethyl acetate layer was distilled off under reduced pressure to get 30 gm of saponified crude extract.

This crude extract (30 g) was subjected to purification by stirring with 150 ml of hexane at room temperature for 1 hr, followed by filtration. 9 g of the precipitate was obtained which was washed with 90 ml ethanol at room temp for 1 hr followed by filtration. The resulting orange crystals were vacuum dried at ambient temperature for 72 hrs. and stored in nitrogen atmosphere The yield of the xanthophyll composition was 4.30 g having xanthophyll content 82.59% by weight (as determined by UV/Vis spectrophotometry). The composition of the product was 83.32% trans-lutein and 15.32% zeaxanthin isomers determined by HPLC analysis.

Example. 3

Marigold oleoresin (50 g) containing 160.07 g/kg xanthophyll content (by spectrophotometric method) was mixed with 25 g potassium hydroxide dissolved in 25 ml 1-propanol. The reaction mixture was heated and maintained at 95.degree.C. for a period of 2 hr. During the reaction stage the sample was taken for analysis of trans-lutein and zeaxanthin content using HPLC during the reaction stage. The reaction mass obtained was stirred with 250 ml distilled water at room temperature. The mixture was taken into a separating funnel and extracted with equal volume of ethyl acetate. This exercise was repeated 5 times. The ethyl acetate layer was collected and washed with distilled water for removing the excess alkali, soapy materials and other water-soluble impurities. The ethyl acetate layer was distilled off under reduced pressure to get 36 g of saponified crude extract.

The resultant crude extract (36.90 g) was subjected to purification by stirring with 185 ml of hexane at room temperature for 1 hr, followed by filtration. 10.33 g of the precipitate was obtained which was washed with 103 ml ethanol at room temp for 1 hr followed by filtration. The resulting orange crystals were vacuum dried at ambient temperature for 72 hrs and stored in nitrogen atmosphere.

The yield of the xanthophyll composition was 7.02 g having xanthophyll content 85.59% by weight (as determined by UV/Vis spectrophotometry). The composition of the product was 86.50. % trans-lutein and 13.2% zeaxanthin isomers determined by HPLC analysis.

Example 4

Marigold oleoresin (52 g) containing 132.2 g/kg xanthophyll content (by spectrophotometric method) was mixed with 26 g potassium hydroxide dissolved in 26 ml 1-propanol. The reaction mixture was heated and maintained at 95.degree.C. for a period of 1 hr. During the reaction stage the sample was taken for analysis of trans-lutein and zeaxanthin content using HPLC. The reaction mass obtained was stirred with 250 ml distilled water) at room temperature. The mixture was taken into a reparatory funnel and extracted with equal volume of ethyl acetate. This exercise was repeated 5 times. The ethyl acetate layer was collected and washed with distilled water for removing the excess alkali, soapy materials and other water-soluble impurities. The ethyl acetate layer was distilled off under reduced pressure to get 30.30 g of saponified crude extract.

The resultant crude extract (30.30 g) was subjected to purification by stirring with 150 ml of hexane at room temperature for 1 hr, followed by filtration. The precipitate (8.00 g) obtained was washed with 80 ml ethanol at room temp for 1 hr followed by filtration. The resulting orange crystals were vacuum dried at ambient temperature for 72 hrs and stored in nitrogen atmosphere The yield of the xanthophyll composition was 4.40 g having xanthophyll content 81.50% by weight (as determined by UV/Vis spectrophotometry). The composition of the product was 86.64% trans-lutein and 11.49% zeaxanthin isomers and trace amounts of other carotenoids as determined by HPLC.

ADVANTAGES OF THE INVENTION

1. The xanthophyll composition contains
(a) macular pigments such as trans-lutein, (R,R)-zeaxanthin and (R,S)-zeaxanthin in a specific ratio.
(b) at least 80% total xanthophylls, out of which the trans-lutein is at least 80% and a remaining portion of about 15-20% typically being zeaxanthin isomers (R,R)- and (R,S)-zeaxanthin respectively.
2. The xanthophyll composition satisfies the safety regulatory considerations because of the use of GRAS reagents and hence safe for human consumption and useful for nutrition and health care.
3. The xanthophyll composition is an one source dietary supplement containing all the essential macular pigments which can help in maintaining eye-health.
4. Many formulators nowadays require active ingredient forms wherein lutein:zeaxanthin isomers ratio is higher than 20:1 which is typical to most of the Marigold Extract products. In order to enhance the zeaxanthin ratio in their finished products supplemental sources of zeaxanthin have to be incorporated in addition to lutein source. In the present invention all the three xanthophylls are present and therefore there is no requirement of addition of any supplementary sources
5. Similarly some formulators seek all three forms of macular carotenoids, i.e. all the 3 pigments found to play a protective role in macular of the retina (namely, lutein, (R,R)-zeaxanthin, (R,S)-zeaxanthin) Currently, it is difficult to get all three carotenoids from one source and hence often formulators need to use 3 different ingredients to make a balanced formulation with all three macular pigments. It is desirable to have a composition comprising trans-lutein and the two zeaxanthin isomers, (R,R)-zeaxanthin and (R,S)-zeaxanthin. However, formulators have needed to use multiple ingredients from more than one source to obtain the three desired xanthophylls. The formulation herein overcomes this drawback.
6. Some formulators are seeking ingredients where lutein:zeaxanthin isomers is in the ratio of 5:1 (in which additionally (R,R)-zeaxanthin (R,S)-zeaxanthin is in the ratio (1:1) to match the ratio of lutein:zeaxanthin isomers in macular pigment.
7. The AREDS II (Age related eye diseases study) study carried out with 4000 subjects assessed the effects of oral supplementation of high doses of macular xanthophylls (i.e., lutein and zeaxanthin) have included the dosage of lutein:zeaxanthin in the supplementation in the ratio 5:1 (10 mg lutein:2 mg zeaxanthin). ref:https://web.emmes.com./study/areds2/resources/areds2_mop.pdf. It is expected that a single ingredient which can provide lutein and zeaxanthin in the ratio 5:1 may be of great benefit to formulators, who are eagerly awaiting the outcome of AREDS II trial. Currently, this objective is met by using multiple ingredients driving up cost, effort and handling of multiple stock items.
8. The xanthophyll composition would enable the development of a standardised composition with the required ratio of lutein:zeaxanthin or lutein:(R,R)-zeaxanthin:(R,S)-zeaxanthin from a single source.

We claim:

1. A xanthophyll composition consisting of an extract of marigold that includes a mixture of converted xanthophylls and obtained from (1) and (2) below, wherein the mixture of converted xanthophylls includes trans-lutein obtained from (1) and (2) below and zeaxanthin isomers obtained from (1) and (2) below, wherein the zeaxanthin isomers obtained from (1) and (2) below consists of (R,R)-zeaxanthin obtained from (1) and (2) below and lutein that has been chemically converted by (1) and (2) below through saponification and isomerization:
  (1) admixing marigold oleoresin obtained by hexane extraction and containing xanthophyll esters with an alkaline solution of 1-propanol, wherein the ratio of alkali and 1-propanol is in the range of 1:0.5 to 1:1 by weight/volume; and
  (2) heating the resultant mass at a temperature in the range 70-100 degree C. for a period in the range of 1 to 5 hrs;
  wherein the lutein that has been chemically converted by (1) and (2) through saponification and isomerization is not found naturally in marigold;

wherein (1) and (2) result in the mixture of converted xanthophylls;

wherein the xanthophyll composition is safe for human consumption and useful for nutrition and health care, the xanthophyll composition comprising: at least 80% by weight total xanthophylls obtained from (1) and (2), of which at least 80% by weight is trans-lutein obtained from (1) and (2), where the ratio of trans-lutein obtained from (1) and (2) to zeaxanthin isomers obtained from (1) and (2) is in the range of about 4:1 to about 6:1, and the ratio of (R,R)-zeaxanthin obtained from (1) and (2) to the lutein that has been chemically converted by (1) and (2) through saponification and isomerization is in the range of 80:20 to 20:80.

2. The xanthophyll composition as claimed in claim 1, wherein the composition contains at least 85% by weight of total xanthophylls, of which the trans-lutein content is at least 85%.

3. The xanthophyll composition as claimed in claim 1, wherein the composition contains at least 85% by weight of total xanthophylls, of which at least 80% by weight being trans-lutein, at least 6% by weight being (R,R)-zeaxanthin and at least 6% by weight being the lutein that has been chemically converted by (1) and (2) through saponification and isomerization.

4. The xanthophyll composition as claimed in claim 1, wherein the composition contains at least 85% by weight trans-lutein and at least 4% by weight (R,R)-zeaxanthin and at least 5% by weight of the lutein that has been chemically converted by (1) and (2) through saponification and isomerization.

5. The xanthophyll composition as claimed in claim 1, wherein the composition containing at least 85% by weight of total xanthophylls, of which at least 80% by weight being trans-lutein, the remaining 15% by weight being zeaxanthin isomers, including (R,R)-zeaxanthin and the lutein that has been chemically converted by (1) and (2) through saponification and isomerization.

6. A process for the preparation of a xanthophyll composition containing macular pigments of trans-lutein, zeaxanthin isomers, including (R,R)-zeaxanthin and (R,S)- zeaxanthin, derived from the plant extract/oleoresin containing xanthophylls/xanthophylls esters which is safe for human consumption and useful for nutrition and health care which comprises:

(a) saponifying and partially isomerising simultaneously xanthophyll esters present in a plant extract/oleoresin containing xanthophyll esters by admixing the extract/oleoresin with alkaline solution of 1-propanol, the ratio of alkali and 1-propanol being in the range of 1:0.5 to 1:1 by weight/volume, heating the resultant mass at a temperature in the range 70-100 degree C. for a period in the range of 1 to 5 hrs to obtain a saponified/isomerised crude concentrate;

(b) admixing the resultant saponified/isomerised crude concentrate obtained in step (a) with water, the ratio of the concentrate and water used being in the range from 1:2 to 1:3 volume/volume, to form a diluted oily mixture;

(c) extracting the diluted oily mixture obtained in step (b) with ethyl acetate, the ratio of diluted oily mixture and ethyl acetate used being in the range of 1:1.5 to 1:2 volume/volume to get an extract containing the xanthophyll composition;

(d) evaporating the composition obtained in step (c) to remove ethyl acetate;

(e) purifying the composition resulting from step (d) by washing first with a non-polar solvent and later with a polar solvent and filtering; and drying the resulting composition under vacuum at a temperature in the range of 40 to 45 degree C. for a period ranging from 48-72 hours.

7. The process as claimed in claim 6, wherein the plant extract/oleoresin containing xanthophyll esters used is derived from marigold flowers.

8. The process as claimed in claim 6, wherein the non-polar solvent used in step (e) is selected from pentane, hexane, and heptane, and the polar solvent used is selected from a lower aliphatic alcohol.

9. The process as claimed in claim 6, further comprising recovering the ethyl acetate used in step (c) for reuse.

10. The process as claimed in claim 6, further comprising storing the resulting composition in an inert atmosphere at 20 degree C.

11. The process as claimed in claim 6, wherein the plant extract/oleoresin containing xanthophyll esters is marigold, where the marigold is the single source of material providing the plant extract/oleoresin containing xanthophyll esters.

12. The process as claimed in claim 6, wherein the non-polar and polar solvents are selected from generally recognized as safe (GRAS) reagents, which are safe for human consumption and suitable for nutrition and health care.

* * * * *